US00PP09948P

United States Patent [19]

Jessel, Jr.

[11] Patent Number: Plant 9,948

[45] Date of Patent: Jul. 8, 1997

[54] CARNATION PLANT VARIETY NAMED 'CFPC MALEA'

[75] Inventor: Walter H. Jessel, Jr., Gonzales, Calif.

[73] Assignee: California Florida Plant Co., L.P., Salinas, Calif.

[21] Appl. No.: 626,532

[22] Filed: Apr. 2, 1996

[51] Int. Cl.[6] ..... A01H 5/00

[52] U.S. Cl. ..... Plt./70.5

[58] Field of Search ..... Plt./70.2, 70.5, Plt./70.6

[56] References Cited

U.S. PATENT DOCUMENTS

P.P. 5,545 8/1985 Hilverda ..... Plt./70.5

P.P. 7,047 10/1989 Barberet-Maiolino et al. ..... Plt./70.5

*Primary Examiner*—Howard J. Locker

*Attorney, Agent, or Firm*—Christie, Parker & Hale, LLP

[57] ABSTRACT

A new variety of carnation plant producing light pink flowers with smooth petal edges and strong stems.

1 Drawing Sheet

SUMMARY OF THE INVENTION

The present invention relates to a new and distinct variety of carnation plant which was originated by me in a controlled breeding program by my crossing as seed parent the variety known as 'CFPC Amethyst' (U.S. Plant Pat. No. 8,122) and as pollen parent an unnamed and unpatented seedling of my creation identified as No. 890013.

Among the novel combination of characteristics possessed by the new variety which distinguishes it are sprays of light pink flowers with smooth petal edges and strong stems. The new variety is also able to produce flower sprays during low light periods. Plants of 'CFPC Malea' exhibit resistance to soil-borne disease such as *Fusarium oxysporum* and *F. graminearum* and root rots such as damping off, water molds and the like. The flowers have a distinctive pink color which is generally retained without fading.

Asexual reproduction by propagation by side shoot cuttings of the new variety as performed in Salinas, Calif., shows that the foregoing and other distinguishing characteristics come true to form and are established and transmitted through succeeding propagations.

The closest commercial cultivar in color to the new cultivar of which I am aware is 'CFPC Serenity', (U.S. Plant Pat. No. 8,249). However, the new variety produces stronger stems and its flowers have a smoother petal edge. Also, 'CFPC Malea' flowers are more pink with less salmon coloration.

BRIEF DESCRIPTION OF ILLUSTRATION

The accompanying illustration shows typical specimens of the vegetative growth and flowers of the new variety depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart. Color designations and color descriptions may deviate from the stated values depending upon varying environmental, seasonal and cultural conditions.

The information provided herein is based on observations of plants grown inside commercial greenhouses at Salinas, Calif. The height of plant and flower and foliage size are established as an average using standard commercial cultural practices. Where terms such as average, normal, ordinary, etc., are used, the characteristics so described are not considered distinguishing.

Name: 'CFPC Malea'.

Classification:

*Botanical.*—Hybrid, *Dianthus caryophyllus.*

*Commercial.*—Carnation, standard spray type.

Parentage:

*Female parent.*—'CFPC Amethyst'.

*Male parent.*—Unnamed seedling (No. 890013).

1. Plant:
   - *Height.*—About 35 inches.
   - *Growing habit.*—Herbaceous, semi-upright.
   - *Blooming habit.*—As a spray.
   - *Blooming season.*—Year round.
   - *Breaking action.*—Good.
   - *Rooting time.*—About 16 days.
   - *Mutation prone.*—No.
   - *Disease resistance.*—Good.
   - *Temperature tolerance.*—Wide range.
2. Foliage:
   - *Color.*—Upper side: Near 137A. Lower side: Near 138A.
   - *Size.*—About 5 inches in length.
   - *Quantity.*—Numerous.
   - *Shape.*—Lanceolate.
   - *Texture.*—Smooth.
   - *Ribs.*—Central, keeled.
   - *Arrangement.*—Bi-lateral along stem.
   - *Stem color.*—Green.
3. Bud:
   - *Shape.*—Ovoid
   - *Color.*—Green.
   - *Length.*—About 1½ inches.
   - *Diameter.*—About ½ inch.
4. Calyx:
   - *Number of sepals.*—About 6.
   - *Length.*—About 1 inch.
   - *Width.*—About ⅓ inch.
   - *Color.*—Outside — near 145A.
   - *Color.*—Inside — near 145C.
5. Bloom:
   - *Shape.*—Round.

*Size.*—Diameter average: About 2½ inches. Depth average: About 1 inch.
*Borne.*—Terminally as a spray.
*Color.*—General tonality: Light pink. Upper side: Near 49D fading to near 36D. Lower side: near 49C fading to near 36C. Center: Near 49C fading to near 36C. Outer petals: Near 49D fading to near 36D.
Keeping Quality: Very good.
Fragrance: Slight.

6. Petals:
*Number.*—About 35.
*Outer petals.*—Length; About 1 inch. Width: About 1¼ inches.
*Central petals.*—Length: About ¾-inch.
Width: About ½ inch.
*Texture.*—Smooth.
*Form.*—Fan shaped.
*Appearance.*—Shiny.

7. Reproductive organs:
*Stamens.*—About 4.
*Anthers.*—About 1/10 inch, color near 164B.
*Filaments.*—About ¼ inch, color near 145A.
*Pistil.*—Number: About 7. Color: Near 155D. Length: 1⅓ inches.
*Stigma.*—Number: About 2. Color: Near 158D.
*Ovary.*—Shape: Conical. Color: Base — tan. Body — green. Apex — light green.
*Fertility.*—Female: Poor. Male: Fair.

I claim:

1. A new and distinct variety of carnation plant substantially as shown and described.

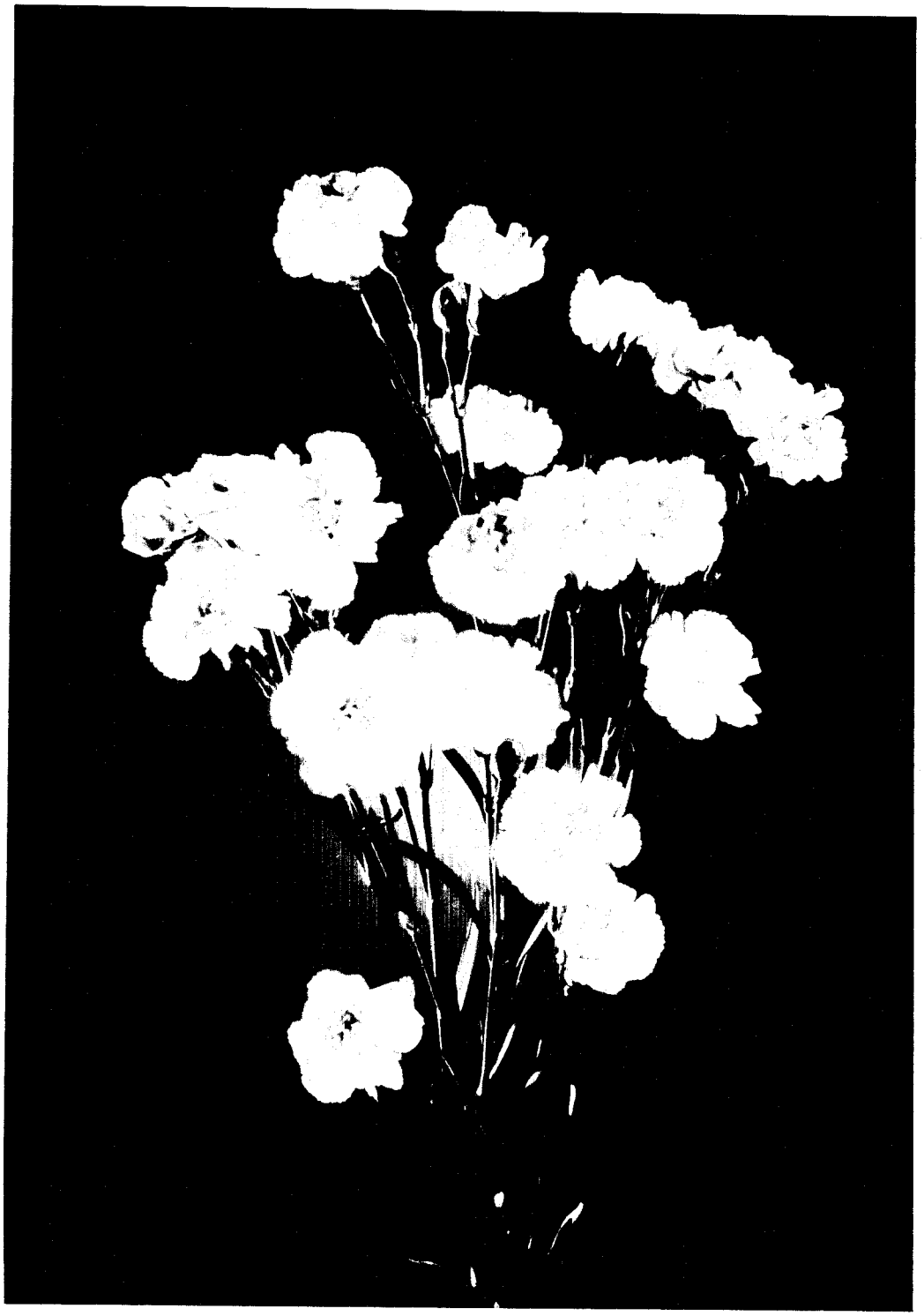

* * * * *